United States Patent
Ahmad et al.

(10) Patent No.: US 12,090,232 B2
(45) Date of Patent: Sep. 17, 2024

(54) ENTERIC SOFTGEL CAPSULES

(71) Applicant: R.P SCHERER TECHNOLOGIES, LLC, Las Vegas, NV (US)

(72) Inventors: Humera Ahmad, Braeside (AU); Jonathan Do, Braeside (AU); Jing Lin, Braeside (AU)

(73) Assignee: R.P. Scherer Technologies, LLC, Las Vegas, NV (US)

( * ) Notice: Subject to any disclaimer, the term of this patent is extended or adjusted under 35 U.S.C. 154(b) by 0 days.

(21) Appl. No.: 16/976,250

(22) PCT Filed: Mar. 15, 2019

(86) PCT No.: PCT/US2019/022477
§ 371 (c)(1),
(2) Date: Aug. 27, 2020

(87) PCT Pub. No.: WO2019/178481
PCT Pub. Date: Sep. 19, 2019

(65) Prior Publication Data
US 2021/0046013 A1 Feb. 18, 2021

Related U.S. Application Data

(60) Provisional application No. 62/643,516, filed on Mar. 15, 2018.

(51) Int. Cl.
*A61J 3/07* (2006.01)
*A23L 29/281* (2016.01)
*A23P 10/30* (2016.01)
*A61K 9/48* (2006.01)

(52) U.S. Cl.
CPC .......... *A61K 9/4825* (2013.01); *A61K 9/4816* (2013.01); *A61K 9/4858* (2013.01)

(58) Field of Classification Search
None
See application file for complete search history.

(56) References Cited

U.S. PATENT DOCUMENTS

| | | | |
|---|---|---|---|
| 6,340,473 B1 | 1/2002 | Tanner et al. | |
| 2010/0087520 A1 | 4/2010 | Liu et al. | |
| 2011/0004506 A1 | 2/2011 | Haug et al. | |
| 2011/0045067 A1 | 2/2011 | Haug et al. | |
| 2013/0189522 A1 | 7/2013 | Fujii et al. | |
| 2013/0259933 A1 | 10/2013 | Kamaguchi et al. | |
| 2015/0335586 A1* | 11/2015 | Baruzzi | A61J 1/067 424/452 |
| 2018/0221288 A1 | 8/2018 | Fukasawa et al. | |

FOREIGN PATENT DOCUMENTS

| | | |
|---|---|---|
| JP | 2009-185022 | 8/2009 |
| RU | 2341290 C2 | 12/2008 |
| WO | 2013100013 A1 | 7/2013 |
| WO | 2017030072 A1 | 2/2017 |

OTHER PUBLICATIONS

Bingsoft fish oil pH (Year: 2022).*
Bingsoft cod oil pH (Year: 2022).*
International Search Report for PCT/US2019/022477 dated May 17, 2019, 2 pgs.
Mulley E.A. et al., Effect of pH and form of the vitamin on its rate of destruction. Journal of Food Science, 1975, 40(5), 990-991.
Romanova E. I et al. // Medical Almanac, 2014, 2 (32), pp. 135-138; retrieved from the Internet: https://elibrary.ru/download/elibrary_21638797_11077706.pdf.
State Pharmacopoeia of the Russian Federation XIII edition, Moscow, 2015, vol. 2, Art. 1.4.1.0005.15 Capsules.

* cited by examiner

*Primary Examiner* — Alton N Pryor
(74) *Attorney, Agent, or Firm* — Lowenstein Sandler LLP

(57) ABSTRACT

Enteric softgel capsules comprise a fill material and an enteric shell composition, characterized in that the enteric nature of the capsules may be achieved without an enteric coating or added conventional enteric polymers.

19 Claims, No Drawings

ENTERIC SOFTGEL CAPSULES

FIELD OF THE INVENTION

The present invention relates to enteric softgel capsules, wherein the gelatin-based shell compositions possess enteric properties without the need for enteric coatings or the addition of conventional enteric polymers.

BACKGROUND OF THE INVENTION

Soft capsules, in particular, soft gelatin capsules (or softgel capsules), provide a dosage form which is more readily accepted by patients, since the capsules are easy to swallow and need not be flavored in order to mask any unpleasant taste of the active agent. Softgel encapsulation of drugs further provides the potential to improve the bioavailability of the pharmaceutical agents. For example, active ingredients may be rapidly released in liquid form as soon as the gelatin shell ruptures.

Efforts have been made to create enteric dosage forms. Enteric dosage forms are designed to protect the contents of the dosage form from gastric conditions. For example, enteric dosage forms may be produced by adding an enteric coating to the surface of a manufactured dosage form such as a tablet or a capsule. Such coatings may be applied through spraying the dosage form, followed by drying the dosage form, usually at elevated temperatures. This method of coating a capsule with an enteric coating may lead to disadvantages in terms of performance and appearance. For example, the capsule may appear rough, the coating may be applied unevenly, and/or the coating can be prone to cracking or flaking off the dosage form. Additionally, the process of applying an enteric coating is very inefficient.

Other enteric dosage forms have been developed in which conventional enteric polymers (i.e., acid-insoluble polymers) are added in the capsule shell. However, the addition of conventional enteric polymers can lead to capsules that are prone to leaking due to insufficient sealing.

Accordingly, there is currently a need for an enteric softgel capsule that does not require either an application of an enteric coating or the addition of conventional enteric polymers in the shell.

Surprisingly, it was found that the gelatin-based shell compositions of the present invention possessed satisfactory enteric properties without the need to apply an enteric coating or incorporate a conventional enteric polymer.

SUMMARY OF THE INVENTION

The present invention is directed to enteric softgel capsules. The enteric softgel capsules comprise (a) a fill material and (2) an enteric shell composition. The enteric softgel capsules according to the present invention do not include either an enteric coating or an added conventional enteric polymer. Accordingly, the enteric shell composition eliminates the need to add an enteric coating, which also minimizes the risk of damaging the capsules during the coating process. The present invention is also directed to a process of making enteric softgel capsules.

In an embodiment, the enteric shell composition comprises (a) a gelatin, (b) a carrageenan, (c) a plasticizer, and (d) a solvent. In another embodiment, the enteric shell composition comprises (a) a gelatin, (b) a carrageenan, (c) a plasticizer, (d) a solvent, and (e) a buffer and/or an alkalizing agent. The present invention is also directed to a process of making enteric softgel capsules.

DETAILED DESCRIPTION OF THE INVENTION

The present invention advances the state of the art by developing enteric oral dosage forms, in particular, enteric softgel capsules, that achieves the advantages associated with the conventional enteric dosage forms without the need to apply an enteric coating or to add a conventional enteric polymer in the capsule shell. The enteric softgel capsules of the present invention do not dissolve in a gastric environment of the stomach, but rather dissolve in the intestines. Such mechanism is beneficial for delivery of active ingredients that may cause stomach irritation or are sensitive to the acidic environment of the stomach.

As used herein, the term is used to refer to the dissolution or disintegration resistant property of a substance such that dissolution or disintegration does not occur in a gastric environment. For example, the embodiments described herein include an enteric shell composition that dissolves in biological, artificial or simulated intestinal fluid rather than in biological, artificial or simulated gastric fluid.

As used herein, "pharmaceutically active ingredient" refers to a drug or compound that may be used in the diagnosis, cure, mitigation, treatment, or prevention of a condition. The term "condition" or conditions refers to those medical conditions that can be treated or prevented by administration to a subject of an effective amount of an active agent. Exemplary non-limiting conditions that may benefit from enteric softgel capsules may include, without limitation, capsules containing lactic acid bacteria, fish oil capsules, proton pump inhibitors, aspirin and similar products.

As used herein, the term "active ingredient" refers to any material that is intended to produce a therapeutic, prophylactic, or other intended effect, whether or not approved by a government agency for that purpose. This term with respect to a specific agent includes the pharmaceutically active agent, and all pharmaceutically acceptable salts, solvates and crystalline forms thereof, where the salts, solvates and crystalline forms are pharmaceutically active.

Any pharmaceutically active ingredient may be used for purposes of the present invention, including both those that are water-soluble and those that are poorly soluble in water. Suitable pharmaceutically active ingredients include, without limitation analgesics and anti-inflammatory agents, antacids, anthelmintic, anti-arrhythmic agents, anti-bacterial agents, anti-coagulants, anti-depressants, anti-diabetics, anti-diarrheal, anti-epileptics, anti-fungal agents, anti-gout agents, anti-hypertensive agents, anti-malarial, anti-migraine agents, anti-muscarinic agents, anti-neoplastic agents and immunosuppressants, anti-protozoal agents, anti-rheumatics, anti-thyroid agents, antivirals, anxiolytics, sedatives, hypnotics and neuroleptics, beta-blockers cardiac inotropic agents, corticosteroids, cough suppressants, cytotoxics, decongestants, diuretics, enzymes, anti-parkinsonian agents, gastro-intestinal agents, histamine receptor antagonists, lipid regulating agents, local anesthetics, neuromuscular agents, nitrates and anti-anginal agents, nutritional agents, opioid analgesics, oral vaccines, proteins, peptides and recombinant drugs, sex hormones and contraceptives, spermicides, stimulants, and combinations thereof.

In some embodiments, the active pharmaceutical ingredient may be selected, without limitations, from the group consisting of dabigatran, dronedarone, ticagrelor, iloperidone, ivacaftor, midostaurine, asimadoline, beclomethasone, apremilast, sapacitabine, linsitinib, abiraterone, vitamin D analogs (e.g., calcifediol, calcitriol, paricalcitol, doxercalciferol), COX-2 inhibitors (e.g., celecoxib, valdecoxib, rofecoxib), tacrolimus, testosterone, lubiprostone, pharmaceutically acceptable salts thereof, and combinations thereof.

In some embodiments, the lipids in the dosage form may be selected, without limitations, from the group consisting of, almond oil, argan oil, avocado oil, borage seed oil, canola oil, cashew oil, castor oil, hydrogenated castor oil, cocoa butter, coconut oil, colza oil, corn oil, cottonseed oil, grape seed oil, hazelnut oil, hemp oil, hydroxylated lecithin, lecithin, linseed oil, macadamia oil, mango butter, manila oil, mongongo nut oil, olive oil, palm kernel oil, palm oil, peanut oil, pecan oil, perilla oil, pine nut oil, pistachio oil, poppy seed oil, pumpkin seed oil, rice bran oil, safflower oil, sesame oil, shea butter, soybean oil, sunflower oil, hydrogenated vegetable oil, walnut oil, and watermelon seed oil. Other oil and fats may include, but not be limited to, fish oil (omega-3), krill oil, animal or vegetable fats, in their hydrogenated form, free fatty acids and mono-, di-, and triglycerides with C8-, C10-, C12-, C14-, C16-, C18-, C20- and C22-fatty acids, and combinations thereof.

According to certain embodiments, active agents may include lipid-lowering agents including, but not limited to, statins (e.g., lovastatin, simvastatin, pravastatin, fluvastatin, atorvastatin, rosuvastatin, and pitavastatin), fibrates (e.g., clofibrate, ciprofibrate, bezafibrate, fenofibrate, and gemfibrozil), niacin, bile acid sequestrants, ezetimibe, lomitapide, phytosterols, and the pharmaceutically acceptable salts, hydrates, solvates and prodrugs thereof, mixtures of any of the foregoing, and the like.

Suitable nutraceutical active agents may include, but are not limited to, 5-hydroxytryptophan, acetyl L-carnitine, alpha lipoic acid, alpha-ketoglutarates, bee products, betaine hydrochloride, bovine cartilage, caffeine, cetyl myristoleate, charcoal, chitosan, choline, chondroitin sulfate, coenzyme Q10, collagen, colostrum, creatine, cyanocobalamin (Vitamin 812), dimethylaminoethanol, fumaric acid, germanium sequioxide, glandular products, glucosamine HCl, glucosamine sulfate, hydroxyl methyl butyrate, immuoglobulin, lactic acid, L-Carnitine, liver products, malic acid, maltose-anhydrous, mannose (d-mannose), methyl sulfonyl methane, phytosterols, picolinic acid, pyruvate, red yeast extract, S-adenosylmethionine, selenium yeast, shark cartilage, theobromine, vanadyl sulfate, and yeast.

Suitable nutritional supplement active agents may include vitamins, minerals, fiber, fatty acids, amino acids, herbal supplements or a combination thereof.

Suitable vitamin active agents may include, but are not limited to, the following: ascorbic acid (Vitamin C), B vitamins, biotin, fat soluble vitamins, folic acid, hydroxycitric acid, inositol, mineral ascorbates, mixed tocopherols, niacin (Vitamin B3), orotic acid, para-aminobenzoic acid, panthothenates, panthothenic acid (Vitamin B5), pyridoxine hydrochloride (Vitamin B6), riboflavin (Vitamin B2), synthetic vitamins, thiamine (Vitamin B1), tocotrienols, vitamin A, vitamin D, vitamin E, vitamin F, vitamin K, vitamin oils and oil soluble vitamins.

Suitable herbal supplement active agents may include, but are not limited to, the following: arnica, bilberry, black cohosh, cat's claw, chamomile, echinacea, evening primrose oil, fenugreek, flaxseed, feverfew, garlic, ginger root, ginko biloba, ginseng, goldenrod, hawthorn, kava-kava, licorice, milk thistle, psyllium, rauowolfia, senna, soybean St. John's wort, saw palmetto, turmeric, valerian.

Minerals active agents may include, but are not limited to, the following: boron, calcium, chelated minerals, chloride, chromium, coated minerals, cobalt, copper, dolomite, iodine, iron, magnesium, manganese, mineral premixes, mineral products, molybdenum, phosphorus, potassium, selenium, sodium, vanadium, malic acid, pyruvate, zinc and other minerals.

Examples of other possible active agents include, but are not limited to, antihistamines (e.g., ranitidine, dimenhydrinate, diphenhydramine, chlorpheniramine and dexchlorpheniramine maleate), non-steroidal anti-inflammatory agents (e.g., aspirin, celecoxib, Cox-2 inhibitors, diclofenac, benoxaprofen, flurbiprofen, fenoprofen, flubufen, indoprofen, piroprofen, carprofen, oxaprozin, pramoprofen, muroprofen, trioxaprofen, suprofen, aminoprofen, fluprofen, bucloxic acid, indomethacin, sulindac, zomepirac, tiopinac, zidometacin, acemetacin, fentiazac, clidanac, oxpinac, meclofenamic acid, flufenamic acid, niflumic acid, tolfenamic acid, diflunisal, flufenisal, piroxicam, sudoxicam, isoxicam, aceclofenac, aloxiprin, azapropazone, benorilate, bromfenac, carprofen, choline magnesium salicylate, diflunisal, etodolac, etoricoxib, faislamine, fenbufen, fenoprofen, flurbiprofen, ibuprofen, indometacin, ketoprofen, ketorolac, lornoxicam, loxoprofen, meloxicam, mefenamic acid, metamizole, methyl salicylate, magnesium salicylate, nabumetone, naproxen, nimesulide, oxyphenbutazone, parecoxib, phenylbutazone, salicyl salicylate, sulindac, sulfinpyrazone, tenoxicam, tiaprofenic acid, tolmetin, pharmaceutically acceptable salts thereof and mixtures thereof) and acetaminophen, anti-emetics (e.g., metoclopramide, methylnaltrexone), anti-epileptics (e.g., phenyloin, meprobmate and nitrazepam), vasodilators (e.g., nifedipine, papaverine, diltiazem and nicardipine), anti-tussive agents and expectorants (e.g. codeine phosphate), anti-asthmatics (e.g. theophylline), antacids, anti-spasmodics (e.g. atropine, scopolamine), antidiabetics (e.g., insulin), diuretics (e.g., ethacrynic acid, bendrofluthiazide), anti-hypotensives (e.g., propranolol, clonidine), antihypertensives (e.g., clonidine, methyldopa), bronchodilatiors (e.g., albuterol), steroids (e.g., hydrocortisone, triamcinolone, prednisone), antibiotics (e.g., tetracycline), antihemorrhoids, hypnotics, psychotropics, antidiarrheals, mucolytics, sedatives, decongestants (e.g. pseudoephedrine), laxatives, vitamins, stimulants (including appetite suppressants such as phenylpropanolamine) and cannabinoids, as well as pharmaceutically acceptable salts, hydrates, solvates, and prodrugs thereof.

The active agent that may also be a benzodiazepine, barbiturate, stimulants, or mixtures thereof. The term "benzodiazepines" refers to a benzodiazepine and drugs that are derivatives of a benzodiazepine that are able to depress the central nervous system. Benzodiazepines include, but are not limited to, alprazolam, bromazepam, chlordiazepoxide, clorazepate, diazepam, estazolam, flurazepam, halazepam, ketazolam, lorazepam, nitrazepam, oxazepam, prazepam, quazepam, temazepam, triazolam, methylphenidate as well as pharmaceutically acceptable salts, hydrates, solvates, prodrugs and mixtures thereof. Benzodiazepine antagonists that can be used as active agent include, but are not limited to, flumazenil as well as pharmaceutically acceptable salts, hydrates, solvates and mixtures thereof.

The ten "barbiturates" refers to sedative-hypnotic drugs derived from barbituric acid (2,4,6-hexahydropyrimidine). Barbiturates include, but are not limited to, amobarbital, aprobarbotal, butabarbital, butalbital, methohexital, mephobarbital, metharbital, pentobarbital, phenobarbital, secobarbital as well as pharmaceutically acceptable salts, hydrates, solvates, prodrugs, and mixtures thereof. Barbiturate antagonists that can be used as active agent include, but are not limited to, amphetamines as well as pharmaceutically acceptable salts, hydrates, solvates and mixtures thereof.

The term "stimulants" includes, but is not limited to, amphetamines such as dextroamphetamine resin complex, dextroamphetamine, methamphetamine, methylphenidate, as well as pharmaceutically acceptable salts, hydrates, and solvates and mixtures thereof. Stimulant antagonists that can be used as active agent include, but are not limited to, benzodiazepines, as well as pharmaceutically acceptable salts, hydrates, solvates and mixtures thereof.

The dosage forms according to the disclosure include various active agents and their pharmaceutically acceptable salts thereof. Pharmaceutically acceptable salts include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like, and metal salts such as sodium salt, potassium salt, cesium salt and the like; alkaline earth metals such as calcium salt, magnesium salt and the like; organic amine salts such as triethylamine salt, pyridine salt, picoline salt, ethanolamine salty triethanolamine salt, dicyclohexylamine salt, N,N'-dibenzylethylenediamine salt and the like.

As used herein, the terms "therapeutically effective" and an "effective amount" refer to the amount of active agent or the rate at which it is administered which is needed to produce a desired therapeutic result.

As used herein, "shell" or "shell composition" refers to the shell of a softgel capsule which encapsulates a fill material.

As used herein, "conventional enteric polymers" refer to, but are not limited to, acrylic and methacrylic acid polymers, which may be available under the tradename EUDRAGIT® and other conventional acid insoluble polymers, e.g., methyl acrylate-methacrylic acid copolymers. Other conventional acid insoluble polymers include, without limitation, cellulose acetate succinate, cellulose acetate phthalate, cellulose acetate butyrate, hydroxypropyl methyl cellulose phthalate, hydroxypropyl methyl cellulose acetate succinate (hypromellose acetate succinate), polyvinyl acetate phthalate (PVAP), algenic acid salts such as sodium alginate and potassium alginate, stearic acid and shellac. In some embodiments, the enteric shell composition of the present invention does not include an acid insoluble polymer. In other words, the enteric shell composition and the enteric softgel capsule are "free or substantially free of conventional enteric polymers."

As used herein, "free or substantially free," refers to a composition that comprises less than about 1% w/w, less than about 0.5% less than about 0.25% w/w, less than about 0.1% w/w, less than about 0.05% w/w, less than about 0.01% w/w, or 0% w/w of said component in the composition.

As used herein, "fill material" or "fill" refers to the composition that is encapsulated by the enteric capsule shell and contains at least one pharmaceutically active ingredient.

As used herein, "enteric capsules" or "enteric softgel capsules" refer to capsules which have enteric properties once the fill material is encapsulated in the shell, and the capsules are dried. No further processing steps are required.

As used herein, "about" in connection with a measured quantity, refers to the normal variations in that measured quantity as expected by one of ordinary skill it the art in making the measurement and exercising a level of care commensurate with the objective of measurement and the precision of the measuring equipment. In certain embodiments, the term "about" includes the recited number ±10%, such that "about 10" would include from 9 to 11.

The term "at least about" in connection with a measured quantity refers to the normal variations in the measured quantity, as expected by one of ordinary skill in the art in making the measurement and exercising a level of care commensurate with the objective of measurement and precisions of the measuring equipment and any quantities higher than that. In certain embodiments, the term "at least about" includes the recited number minus 10% and any quantity that is higher such that "at least about 10" would include 9 and anything greater than 9. This term can also be expressed as "about 10 or more." Similarly, the term "less than about" typically includes the recited number plus 10% and any quantity that is lower such that "less than about 10" would include 11 and anything less than 11. This term can also be expressed as "about 10 or less."

As used herein, "a," "an" or "the" refers to one or more, unless otherwise specified. Thus, for example, reference to "an excipient" includes a single excipient as well as a mixture of two or more different excipients and the like.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

The use of any and all examples, or exemplary language (e.g., "such as") provided here is intended merely to illuminate certain materials and methods and does not pose a limitation on scope. No language in the specification should be construed as indicating any non-claimed element as essential to the practice disclosed materials and methods.

According to a first embodiment, an enteric softgel capsule comprises (a) a fill material and (b) an enteric shell composition, wherein the fill material comprises at least one pharmaceutically active ingredient, wherein the enteric shell composition comprises a gelatin, a carrageenan, a plasticizer, and a solvent, wherein the enteric shell composition is free of conventional enteric polymers.

According to a second embodiment, an enteric softgel capsule comprises (a) a fill material and (b) an enteric shell composition, wherein the fill material comprises at least one pharmaceutically active ingredient, wherein the enteric shell composition comprises a gelatin, a carrageenan, a plasticizer, a solvent, and, optionally, a buffer and/or an alkalizing agent, wherein the enteric shell composition is free of conventional enteric polymers.

Suitable fill materials comprise at least one pharmaceutically active ingredient and can be made according to known methods. In addition to the at least one pharmaceutically cave ingredient, suitable fill materials may comprise additional fill components such as flavoring agents, sweetening agents, coloring agents and fillers or other pharmaceutically acceptable excipients or additives such as synthetic dyes and mineral oxides. Suitable amounts of pharmaceutically active ingredient and pharmaceutically acceptable excipients can be readily determined by one of ordinary skill in the art. Notably, it has been found that dosage forms comprising enteric softgel capsules as described herein and a fill composition having a pH of about 2.5 to about 6.5, or about 3.0 to about 6.0, or about 3.5 to about 5.5 exhibit suitable stability. According to embodiments, the fill composition can be an alkali fill, for example, esomeprazole.

In an embodiment, the gelatin in the enteric shell composition may include, but is not limited to, Type A gelatin, Type B gelatin, a hide gelatin, a fish gelatin, porcine gelatin and/or a bone gelatin used alone or in combination. In an embodiment, the gelatin is Type A high bloom gelatin. In an embodiment, the gelatin is Type B high bloom gelatin. In one embodiment, the gelatin is a 250 bloom gelatin. In another embodiment, there is only one type of gelatin. In yet another embodiment, the gelatin is a combination of at least two types of gelatins. In an embodiment, the amount of gelatin the enteric shell composition is about 10% w/w to about 30% w/w, more preferably from about 15% w/w to about 30% w/w, and most preferably from about 25% to about 30% w/w.

In an embodiment, the carrageenan in the enteric shell composition may be kappa-carrageenan, iota-carrageenan, lambda-carrageenan and mixtures thereof. According to one embodiment, the carrageenan is kappa-carrageenan. According to another embodiment, the carrageenan is iota-carrageenan. In an embodiment, the amount of the carrageenan the enteric shell composition is about 2% w/w to about 10% w/w, more preferably from about 2% w/w to about 8% w/w, and most preferably from about 2% to about 5% w/w.

In an embodiment, the plasticizer in the enteric shell composition may include glycerol, glycerin, sorbitol or a mixture thereof. Other suitable plasticizers may include, but not be limited to, sugar alcohol plasticizer such as isomalt, maltitol, xylitol, erythritol, adonitol, dulcitol, pentaerythritol, or mannitol; or polyol plasticizer such as diglycerin, ethylene glycol, diethylene glycol, triethyleneglycol, tetraethylene glycol, dipropylene glycol, a polyethylene glycol up to 10,000 MW, neopentyl glycol, propylene glycol, 1,3-propanediol, 2-methyl-1,3-propanediol, trimethylolpropane, a polyether polyol, ethanol amines; and mixtures thereof. Other exemplary plasticizers may also include, without limitations, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, citrate ester-type plasticizers, and triacetin. Such plasticizers may include 1,2-butylene glycol, 2,3-butylene glycol, styrene glycol, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutyl sebacate, acetyltributylcitrate, triethyl citrate, glyceryl monostearate, polysorbate 80, acetyl triethyl citrate, tributyl citrate and allyl glycolate, and mixtures thereof. In an embodiment, the amount of plasticizer in the enteric shell composition is about 10% w/w to about 35% w/w, more preferably from about 10% w/w to about 30% w/w, and most preferably from about 15% w/w to about 28% w/w.

In an embodiment, the enteric shell composition and the enteric softgel capsule capsule may be free or substantially free of conventional enteric polymers.

In an embodiment, the enteric shell composition and the enteric softgel capsule may be free or substantially free of divalent cation salts, such as $Ca^{++}$ (e.g., $CaCl_2$) or $Mg^{++}$ (e.g., $MgCl_2$).

In an embodiment, the solvent in the enteric shell composition may be or include water. In an embodiment, the amount of solvent in the capsule shell is about 20% w/w to about 50% more preferably from about 30% w/w to about 50% w/w, and most preferably from about 35% w/w to about 50 w/w.

In an embodiment, the enteric shell composition also includes a buffer and/or an alkalizing agent. A suitable buffer and/or alkalizing agent includes, but is not limited to, ammonium hydroxide, sodium hydroxide, sodium carbonate, sodium citrate, trisodium phosphate and/or disodium phosphate. In one embodiment, the buffer is disodium phosphate. In an embodiment, the amount of the buffer in the enteric shell composition is about 0.1% w/w to about 3% w/w, more preferably from about 0.5% w/w to about 1% w/w, and most preferably from about 0.5% w/w to about 0.9% w/w.

In an embodiment, the enteric shell composition may optionally comprise additional agents such as coloring agents, flavorings agents, sweetening agents, fillers, antioxidants, diluents or other pharmaceutically acceptable excipients or additives such as synthetic dyes and mineral oxides.

Exemplary suitable coloring agents may include, but are not limited to, colors such as e.g., white, black, yellow, blue, green, pink, red, orange, violet, indigo, and brown. In specific embodiments, the color of the dosage form can indicate the contents (e.g., one or more active ingredients) contained therein.

Exemplary suitable flavoring agents may include, but are not limited to, "flavor extract" obtained by extracting a part of a raw material, e.g., animal or plant material, often by using a solvent such as ethanol or water; natural essences obtained by extracting essential oils from the blossoms, fruit, roots, etc., or from the whole plants.

Additional exemplary flavoring agents that may be in the dosage form may include, but are not limited to, breath freshening compounds like menthol, spearmint, and cinnamon, coffee beans, other flavors or fragrances such as fruit flavors cherry, orange, grape, etc.), especially those used for oral hygiene, as well as actives used in dental and oral cleansing such as quaternary ammonium bases. The effect of flavors may be enhanced using flavor enhancers like tartaric acid, citric acid, vanillin, or the like.

Exemplary sweetening agents may include, but are not limited to, one or more artificial sweeteners, one or more natural sweeteners, or a combination thereof. Artificial sweeteners include, e.g., acesulfame and its various salts such as the potassium salt (available as Sunett®), alitame, aspartame (available as NutraSweet® and Equal®), salt of aspartame acesulfame (available as Twinsweet®), neohesperidin dihydrochalcone, naringin dihydrochalcone, dihydrochalcone compounds, neotame, sodium cyclamate, saccharin and its various salts such as the sodium salt (available as Sweet'N Low®), stevia, chloro derivatives of sucrose such as sucralose (available as Kaltame® and Splenda®), and mogrosides. Natural sweeteners include, e.g., glucose, dextrose, invert sugar, fructose, sucrose, glycyrrhizin; monoammonium glycyrrhizinate (sold under the trade name MagnaSweet®); Stevia rebaudiana (Stevioside) natural intensive sweeteners, such as Lo Han Kuo, polyols such as sorbitol, mannitol, xylitol, erythritol, and the like.

The enteric softgel capsule according to an embodiment may remain intact for about one hour, about two hours, about three hours, about four hours, about five hours, or longer than about 1-5 hours in acidic medium and may disintegrate in intestinal fluid in about 120 minutes or less, or about 100 minutes or less, or about 80 minutes or less, or about 60 minutes or less, or about minutes or less, or about 30 minutes of less, or about 10 minutes or less, or about 5 minutes or less. The disintegration may be measured using the in Line BP/USP method. For example, using USP <701> Disintegration test, the softgel capsules can be disintegrated in a basket-rack assembly. The basket-rack assembly can include six-open ended transparent tubes, each 77.5±25 mm long and having an inside diameter of 20.7 to 23 mm and a wall 1.0 to 2.8 mm thick; the tubes are held in a vertical position by two plates, each 88 to 92 min in diameter and 5 to 8.5 in thickness, with six holes, each 22 to 26 mm in diameter, equidistant from the center of the plate and equally spaced from one another. Attached to the under surface of the lower plate is a woven stainless steel weave with 1.8- to 2.2-mm apertures and with a wire diameter of 0.57 to 0.66 mm. The parts of the apparatus are assembled and rigidly held by means of three bolts passing through the two plates. A suitable means is provided to suspend the basket-rack assembly from the raising and lowering device using a point on its axis. The use of disks is permitted only where specified or allowed in the monograph. Additionally, a removable wire cloth having the aforementioned weave and diameter specifications is attached to the surface of the upper plate of the basket-rack assembly.

One (1) dosage unit is placed in each of six tubes of the basket of a basket-rack assembly and, if necessary, a disk is added. Each enteric softgel capsule is immersed in 0.1 N HCl, which is maintained at a temperature of 37° C.±2° C. After 120 minutes, or 100 minutes, or 80 minutes, or 60 minutes, or 45 minutes, or 30 minutes, or 10 minutes, or 5 minutes, the basket is lifted from the fluid, and the enteric softgel capsules are observed to see if they have all disintegrated completely. If 1 or 2 enteric softgel capsules fail to disintegrate completely, the test is repeated on 12 additional enteric softgel capsules. The requirement is met if not fewer than 16 of the total of 18 enteric softgel capsules tested are disintegrated.

Encapsulation of the fill material can be accomplished using any conventional manner. As an example, a rotary die encapsulation may be used. In embodiments, the encapsulation process can use equipment and processes for vegetarian capsules due to the relatively high melting point of the gel in the enteric softgel capsule.

According to an embodiment, an enteric softgel capsule is prepared by a process comprising the steps of: (a) preparing the fill material, said fill material comprising at least one pharmaceutically active ingredient; and (b) encapsulating the fill material of step (a) in an enteric shell composition. The encapsulation process according to step (b) may further comprise a sub-step of preparing the enteric shell composition by, for example, cooking a gelatin wherein the temperature is about 50° C. to about 65° C. to produce a bubble free gel, raising the temperature of the gelatin to about 70° C. to about 90° C., preferably about 80° C. to about 90° C., and dispersing a premix of carrageenan and glycerol (glycerin) in the gelatin under agitation producing a clear gel solution.

In an embodiment, the enteric shell composition comprises (a) a carrageenan, (b) a gelatin, (c) a plasticizer, (d) a solvent, and optionally (e) a buffer and/or alkalizing agent.

In an embodiment, the enteric shell composition consists essentially of (a) a carrageenan, (b) a gelatin, (c) a plasticizer, (d) a solvent, and optionally (e) a buffer and/or alkalizing agent.

In an embodiment, the enteric shell composition consists of (a) a carrageenan, (b) a gelatin, (c) a plasticizer, (d) a solvent, and optionally (e) a buffer and/or alkalizing agent.

In an embodiment, the enteric softgel capsule composition comprises (a) about 1% w/w to about 20% w/w, or about 1.5% w/w to about 15 w/w, or about 2% w/w to about 10% w/w of a carrageenan, (b) about 1% to about 50% w/w, or about 5% w/w to about 40% w/w, or about 10% w/w to about 30% w/w of a gelatin, (c) about 1% w/w to about 55% w/w, or about 5% w/w about 45% w/w, about 10% w/w to about 35% w/w of a plasticizer, (d) about 5% w/w to about 60% w/w, or about 10% w/w to about 55% w/w, or about 20% w/w to about 50% of a solvent, and optionally (e) about 0.01% w/w to about 10% w/w, or about 0.05% w/w to about 5% w/w, or about 0.1% w/w to about 3% w/w of a buffer and/or alkalizing agent.

In an embodiment, the enteric softgel capsule composition consists essentially of (a) about 1% w/w to about 20% w/w, or about 1.5% t about 15% w/w, or about 2% w/w to about 10% w/w of a carrageenan, (b) about 1% w/w to about 50% w/w, or about 5% w/w to about 40% w/w, about 10% w/w to about 30% w/w of a gelatin, (c) about 1% w/w to about 55% w/w, or about 5% w/w to about 45% w/w, about 10% w/w to about 35% w/w of a plasticizer, (d) about 5% w/w to about 60% w/w, or about 10% w/w to about 55% w/w, or about 20% w/w to about 50% w/w of a solvent, and optionally (e) about 0.01% w/w to about 10% w/w, or about 0.05% w/w to about 5% w/w, or about 0.1% w/w to about 3% w/w of a buffer and/or alkalizing agent.

In an embodiment, the enteric softgel capsule composition consists of (a) about 1% w/w to about 20% w/w, or about 1.5% w/w to about 15% w/w, or about 2% w/w to about 10% w/w of a carrageenan, (b) about 1% w/w to about 50% w/w, or about 5% w/w to about 40% w/w, or about 10% w/w to about 30% w/w of a gelatin, (c) about 1% w/w to about 55% w/w, or about 5% w/w to about 45% w/w, about 10% w/w to about 35% w/w of a plasticizer, (d) about 5% w/w to about 60% w/w, or about 10% w/w to about 55% w/w, about 20% w/w to about 50% w/w of a solvent, and optionally (e) about 0.01% w/w to about 10% w/w, or about 0.05% w/w to about 5% w/w, or about 0.1% w/w to about 3% w/w of a buffer and/or alkalizing agent.

EXAMPLES

Specific embodiments will now be demonstrated by reference to the following examples. It should be understood that these examples are disclosed solely by way of illustrating the invention and should not be taken in any way to limit the scope of the present invention.

Example 1

An enteric softgel capsule was prepared having the composition set forth in Table 1 below. In a gel melter, water, glycerin and gelatin were added. The mixture was stirred and heated to 70° C. to 80° C. under vacuum (standard gel process), then mixed and heated to 82° C. to 85° C. Next a premix of carrageenan and glycerin at room temperature were added. The mixture was again heated to 82° C. to 85° C. with vacuum to deaerate. The mixture was discharged from the melter, and colors and flavors were bicycled in. Finally the mixture was encapsulated.

TABLE 1

| | |
|---|---|
| Gelatin (250 bloom hide/bone) | 26.28% w/w |
| Carrageenan (Iota) | 2.89% w/w |
| Glycerin | 24.48% w/w |
| Water, purified | 45.88% w/w |
| Additional Additives including coloring and flavoring agents | 0.47% w/w |
| Total | 100% |

Immediately after the capsules were dried, the samples were subjected to enteric disintegration testing in 0.1 N HCl. The capsules passed the dissolution time tests. The capsules were also stored in HDPE bottles and stability tested at 25° C./60% RH and 30° C./75% RH. At 0, 2, 3 and 6 months, the capsules passed DT tests in both 0.1 N HCl and phosphate buffer at both temperatures in accordance with USP/BP/EP requirements (see, e.g., USP disintegration test described above).

TABLE 2

| Parameter 30° C./75% | 0 months | 1 months | 2 months | 3 months | 6 months | 14 months |
|---|---|---|---|---|---|---|
| Appearance | Good | Good | Good | Good | Good | Good |
| Seam Integrity | Good | Good | Good | Good | Good | Good |
| Equilibrium Relative Humidity (%) | 12.68% | 18.20% | 15.77% | 10.56% | 11.40% | 15.36% |
| Disintegration Time (in 0.1N HCL) | Pass | Pass | Pass | Pass | Pass | Pass |
| Disintegration Time (in phosphate buffer) | Pass | Pass | Pass | Pass | Pass | Pass |

COMPARATIVE EXAMPLES

Enteric softgel capsules were prepared having the compositions set forth in Table 2 below by the method set forth above.

TABLE 3

| | Comp. Ex. A | Comp. Ex. B | Comp. Ex. C | Comp. Ex. D |
|---|---|---|---|---|
| Gelatin (HB, 250 bloom hide/bone) | 22.4% w/w | 22.19% w/w | 25.17% w/w | 28.2% w/w |
| Carrageenan (Iota, E407) | 3.27% w/w | 3.24% w/w | 2.82% w/w | 2.75% w/w |
| Glycerin (B.P.) | 22.4% w/w | 22.19% w/w | 24.37% w/w | 23.6% w/w |
| Water, purified (BP) | 47.6% w/w | 47.12% w/w | 46.02% w/w | 44.8% w/w |
| Hydroxypropyl Starch | 3.73% w/w | 3.70% w/w | 0.00% w/w | 0.00% w/w |
| Disodium Phosphate | 0.642% w/w | 0.64% w/w | 0.69% w/w | 0.68% w/w |
| Additional Additives including coloring and flavoring agents | 0% w/w | 0.91% w/w | 0.91% w/w | 0% w/w |
| Total | 100% Able to encapsulate, however did not meet DT at t = 0 due to insufficient capsule sealing | 100% Less suitable for encapsulation due to weak ribbon | 100% Able to encapsulate, however did not meet DT at t = 0 due to insufficient capsule sealing | 100% Less suitable for encapsulation due to undissolved gelatin |

Comp. Ex. B and Comp. Ex. D failed to provide a composition that could be successfully encapsulated. Comp. Ex. A and Comp. Ex. C were able to be encapsulated. Immediately after the capsules were dried, the samples were subjected to enteric disintegration testing in 0.1 N HCl (see, e.g., USP disintegration method described above). Both sets of capsules failed the disintegration time tests. Some of the capsules were placed in 35° C. for annealing for 4 days. All capsules passed the DT tests after the annealing. It shows that the capsule seals (hot melt junctions) require a period of further thermal equilibrium to develop the binding strength.

A critical aspect of the enteric softgel technology is manufacturing process. The acid resistance relies on strong capsule seal which is commonly known as the weakest part of a softgel capsule. Strong seal can only be achieved by a combination of strong gel, skillful design of the die tooling and control of the process parameters during encapsulation. Stronger gel was achieved by using high bloom gelatin and optimizing the gel formulation. In Example 1, the encapsulation of enteric softgels uses a rotary die process. However, the ribbon generation utilizes a similar process to Vegicap gel, i.e., melt on demand which is different from gelatin process.

What is claimed is:

1. A stable enteric softgel capsule comprising:
   (a) a fill material; and
   (b) an enteric shell composition,
   wherein the stable enteric softgel capsule has been dried,
   wherein the fill material comprises at least one pharmaceutically active ingredient,
   wherein, prior to the enteric softgel capsule being dried, the enteric shell composition comprises 2.75% w/w to about 10% w/w of a polysaccharide, wherein the polysaccharide is a carrageenan and is the sole polysaccharide in the enteric shell composition, and wherein the carrageenan is iota carrageenan and does not comprise kappa carrageenan,
   about 10% w/w to about 30% w/w of a gelatin,
   about 10% w/w to about 35% w/w of a plasticizer, and
   about 20% w/w to about 50 w/w of a solvent, and
   wherein the enteric softgel capsule is free of conventional enteric polymers,
   wherein the enteric softgel capsule is stable for 0 up to 6 months at 25° C./60% relative humidity (RH) and 30° C./75% RH.

2. The enteric softgel capsule of claim 1, wherein the gelatin comprises at least one of Type A gelatin, Type B gelatin and mixtures thereof.

3. The enteric softgel capsule of claim 1, wherein the gelatin comprises at least one of fish gelatin, hide gelatin, bone gelatin and mixtures thereof.

4. The enteric softgel capsule of claim 2, wherein the gelatin is the Type B high bloom gelatin.

5. The enteric softgel capsule of claim 2, wherein the gelatin is the Type A high bloom gelatin.

6. The enteric softgel capsule of claim 1, wherein the plasticizer comprises at least one of glycerol, glycerin, sorbitol and mixtures thereof.

7. The enteric softgel capsule of claim 6, wherein the plasticizer is glycerol.

8. The enteric softgel capsule of claim 1, wherein the solvent is water.

9. The enteric softgel capsule of claim 1 further comprising a buffer.

10. The enteric softgel capsule of claim 1, wherein the capsule disintegrates in about one hour, about two hours, about three hours, about four hours, or about five hours in an acidic medium.

11. The enteric softgel capsule of claim 1, therein the fill material has a pH of about 2.5 to about 6.5, or about 3.0 to about 6.0, or about 3.5 to about 5.5.

12. A process of preparing an enteric softgel capsule according to claim 1 comprising the steps of:
(a) preparing a fill material; and
(b) encapsulating the fill material with the enteric shell composition.

13. The process of claim 12, further comprising preparing the enteric shell composition by adding the solvent, the glycerin and the gelatin to a melter to form a mixture.

14. The process of claim 13, comprising mixing the mixture at a temperature of about 70° C. to about 80° C. under vacuum.

15. The process of claim 14, further comprising heating the mixture to a temperature of about 82° C. to about 85° C.

16. The process of claim 13, further comprising combining the mixture with a premix of the carrageenan and the plasticizer.

17. The process of claim 12, further comprising, drying the enteric shell composition.

18. A stable enteric softgel capsule comprising:
(a) a fill material; and
(b) an enteric shell composition,
wherein the stable enteric softgel capsule has been dried,
   wherein the fill material comprises at least one pharmaceutically active ingredient,
   wherein, prior to the enteric softgel capsule being dried, the enteric shell composition comprises 2.75% w/w to about 10% w/w of a polysaccharide, wherein the polysaccharide is a carrageenan and is the sole polysaccharide in the enteric shell composition, and wherein the carrageenan is iota carrageenan and does not comprise kappa carrageenan,
about 10% w/w to about 30% w/w of a gelatin,
about 10% w/w to about 35% w/w of a plasticizer,
about 20% w/w to about 50 w/w of a solvent, and
about 0.1% w/w to about 3% w/w of a buffer and/or an alkalizing agent, and
wherein the enteric softgel capsule is free of conventional enteric polymers,
wherein the enteric softgel capsule is stable for 0 up to 6 months at 25° C./60% RH and 30° C./75% RH.

19. The enteric softgel capsule of claim 18, wherein the buffer is disodium phosphate.

* * * * *